(12) United States Patent
Wang et al.

(10) Patent No.: US 6,905,999 B2
(45) Date of Patent: Jun. 14, 2005

(54) POLYMERIZATION OF OLEFINS

(75) Inventors: Ying Wang, Wilmington, DE (US);
Steven Dale Ittel, Wilmington, DE (US)

(73) Assignee: E. I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/791,242

(22) Filed: Mar. 2, 2004

(65) Prior Publication Data

US 2004/0171481 A1 Sep. 2, 2004

Related U.S. Application Data

(62) Division of application No. 09/801,034, filed on Mar. 7, 2001, now Pat. No. 6,562,751.
(60) Provisional application No. 60/188,663, filed on Mar. 10, 2000.

(51) Int. Cl.[7] .............................. B01J 31/38; C08F 4/44
(52) U.S. Cl. ........................ 502/155; 502/167; 526/172
(58) Field of Search ............................... 502/155, 167; 526/172

(56) References Cited

U.S. PATENT DOCUMENTS

| | | | |
|---|---|---|---|
| 3,929,848 | A | 12/1975 | Bader et al. |
| 4,206,139 | A | 6/1980 | Idelson et al. |
| 5,714,556 | A | 2/1998 | Johnson et al. |
| 5,880,241 | A | 3/1999 | Brookhart et al. |
| 6,060,569 | A | 5/2000 | Bennett et al. |
| 6,174,975 | B1 | 1/2001 | Johnson et al. |

FOREIGN PATENT DOCUMENTS

| | | |
|---|---|---|
| EP | 08/4005 | 10/1998 |
| WO | WO 98/42664 | 10/1998 |
| WO | WO 98/42665 | 10/1998 |

OTHER PUBLICATIONS de Blas et al., Synthesis and Characterization of Ti(IV) Complexes with Silylated Schiff Bases, Synth. React. Inorg. Met.–Org. Chem., 21(8), 1273–1298 (1997).*

Rehder et al., The preparation and synthetic potential of chlorovandium (V and IV) complexes supported by enamines and bis(enamines) Inorganica Chimica Acta 267 (1998) pp. 229–238.*

Rehder et al., Models for Vanadate–Dependent Haloperoxidases: Vanadium Complexes with O4N–Donor Sets, Chem. Ber./Recueil 1997, 130, pp. 651–657.*

Chatterjee, D. et al., Oxidation of organic substrates catalyzed by novel mixed–ligand manganese(III) complexes, Journal of Molecular Catalysis A: Chemical, 2001. p. 41–45, vol. 169, Elsevier Science B.V.

Alyea E.C. et aL., Schiff base complexes of mono(cyclopentadienyl) titanium(IV), Inorg. Nucl. Chem. Letters, 1977, p. 587–590, vol. 13, Pergamon Press.

Chatterjee, D. et al., Oxidation of organic substrates catalyzed by novel mixed–ligand chromium(III) complexes, 2000, p. 217–222, vol. 71(2), Kluwer Academic Publishers.

Jezierski, Adam, Selenium Oxychloride as an Effective Chlorinating Agent and Solvent for Vanadium(IV) Complexes. An ESR Study, Inorganica Chimica Acta, 1985, p. L1–L2, vol. 98, Elsevier Sequoia.

de Blas, A. et al., Synthesis and characterization of titanium(IV) complexes with silylated schiff bases, Synth. React. Inorg. Met.–Org. Chem., 1991, p. 1273–1298, vol. 21(8), Marcel Dekker, Inc.

Schmidt, H. et al., The preparation and synthetic potential of chlorovanadium (V and IV) complexes supported by enamines and bis(enamines), Inorganica Chimica Acta, 1998, p. 229–238, vol. 267, Elsevier Sciences S.A.

Bashirpoor, M. et al., Models for vanadate–dependent haloperoxidases: vanadium complexes with 04N–Donor Sets, Chem. Ber., 1997, p. 651–657, vol. 130.

* cited by examiner

Primary Examiner—Robert D. Harlan

(57) ABSTRACT

Olefins, such as ethylene, are polymerized using as a polymerization catalyst a complex of a selected transition metal with an anionic ligand that has at least three atoms that may coordinate to the transition metal. Also disclosed are the above selected transition metal complexes, and intermediates thereto.

4 Claims, No Drawings

POLYMERIZATION OF OLEFINS

CROSS-REFERENCE TO RELATED APPLICATION

This application is a division of and claims priority under 35 U.S.C. §119 from U.S. Provisional Application Ser. No. 60/188,663 (filed Mar. 10, 2000) and U.S. application Ser. No. 09/801,034 (filed Mar. 7, 2001) now U.S. Pat. No. 6,562,751, which is incorporated by reference herein for all purposes as if fully set forth.

FIELD OF THE INVENTION

Olefins, such as ethylene, are polymerized using as a polymerization catalyst selected transition metal complexes of anionic ligands having three donor atoms that may coordinate to the transition metal.

TECHNICAL BACKGROUND

Polymers of olefins are important items of commerce, and these polymers are used in a myriad of ways, from low molecular weight polyolefins being used in lubricants and waxes, to higher molecular weight grades being used for fiber, films, molding resins, elastomers, etc.

Olefins may be polymerized by a variety of transition metal containing catalysts, for example metallocene and Ziegler-Natta type catalysts. More recently, other types of transition metal containing polymerization catalysts have been discovered, in which the transition metal atom is complexed to a neutral or monoanionic ligand. See, for instance, U.S. Pat. No. 5,714,556, U.S. Pat. No. 5,880,241, U.S. Pat. No. 6,060,569, U.S. Pat. No. 6,174,975, WO 9842664 and WO 9842665, all of which are incorporated by reference herein for all purposes as if fully set forth. Each type of polymerization catalyst has its advantages and disadvantages, and due the commercial importance of polyolefins, new polymerization catalysts are constantly being sought.

SUMMARY OF THE INVENTION

One aspect of the present invention concerns a first process for the polymerization of olefins, comprising the step of contacting, at a temperature of about −100° C. to about +200° C., one or more monomers selected from the group consisting of ethylene and an olefin of the formula $H_2C=CH(CH_2)_nH$ (XXII), and a Cr, Mn, V, Ti, Zr or Hf complex of an anion of the formula (I)

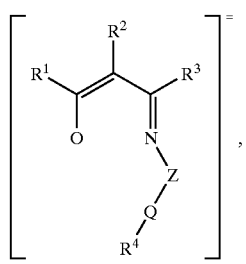

wherein:

$R^1$ is hydrocarbyl or substituted hydrocarbyl, $R^2$ is hydrogen, hydrocarbyl or substituted hydrocarbyl, and $R^3$ is hydrogen, hydrocarbyl, substituted hydrocarbyl or a functional group, provided that $R^1$ and $R^2$ taken together may be ortho-arylene or substituted ortho-arylene, or $R^1$, $R^2$ and $R^3$ taken together may form one or more rings;

Z is a bridging group of the formula (II), (III) or (IV)

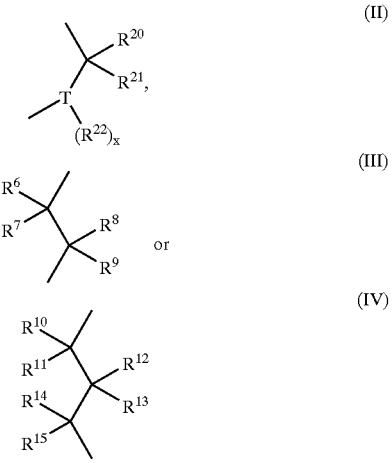

Q is nitrogen, oxygen, phosphorous or sulfur, provided that when Z is (II), Q is oxygen;

$R^4$ is hydrogen, hydrocarbyl or substituted hydrocarbyl, provided that when Q is oxygen or sulfur $R^4$ is not present;

$R^6$ is hydrogen, hydrocarbyl or substituted hydrocarbyl, provided that $R^3$ and $R^6$ together may form a ring;

$R^7$ is hydrogen, hydrocarbyl or substituted hydrocarbyl, provided that $R^3$, $R^6$ and $R^7$ together may form an aromatic ring, or $R^6$ and $R^7$ taken together may form a ring;

$R^8$ is hydrogen, hydrocarbyl or substituted hydrocarbyl;

$R^9$ is hydrogen, hydrocarbyl or substituted hydrocarbyl, provided that $R^4$ and $R^9$ taken together may be part of a double bond to an imino nitrogen atom, or $R^8$ and $R^9$ taken together may form a carbonyl with the carbon to which they are attached, or $R^8$ and $R^9$ taken together may form a ring, or $R^4$ and $R^9$ taken together may form a ring, or $R^4$, $R^8$ and $R^9$ taken together may form a ring, or $R^6$, $R^7$, $R^8$ and $R^9$ taken together may form an aromatic ring;

$R^{10}$, $R^{11}$, $R^{12}$ and $R^{13}$ are each independently hydrogen, hydrocarbyl or substituted hydrocarbyl, provided that $R^{10}$, $R^{11}$, $R^{12}$ and $R^{13}$ taken together may be ortho-arylene;

$R^{14}$ and $R^{15}$ are each independently hydrogen, hydrocarbyl or substituted hydrocarbyl, provided that $R^{14}$ and $R^{15}$ taken together may form a carbonyl with the carbon to which they are attached, or $R^{12}$, $R^{13}$, $R^{14}$, and $R^{15}$ taken together may form an o-arylene group, or $R^{10}$, $R^{11}$, $R^{12}$, $R^{13}$, $R^{14}$, and $R^{15}$ taken together may form a fused aromatic ring system, or $R^{13}$ and $R^{14}$ taken together may form a ring;

$R^{20}$ and $R^{21}$ are each independently hydrogen, hydrocarbyl or substituted hydrocarbyl, or $R^{20}$ and $R^{21}$ taken together may form a ring;

each $R^{22}$ is individually hydrocarbyl, oxygen or alkoxy, provided that when $R^{22}$ is oxygen, two of $R^{22}$ are taken together to form T=O;

n is an integer of 1 or more;

T is phosphorous or sulfur whose oxidation state is 3 or greater; and x is equal to the oxidation state of T minus 2.

Another aspect of the present invention concerns a second process for the polymerization of olefins, comprising the step of contacting, at a temperature of about −100° C. to about +200° C., one or more monomers selected from the group consisting of ethylene and $H_2C=CH(CH_2)_nH$ (XXII), with a compound of the formula (V)

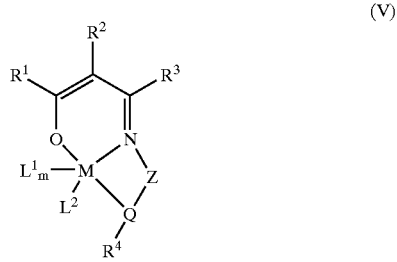

wherein:
$R^1$, $R^2$, $R^3$, $R^4$, Q, Z (and all R groups associated with Z), M and m are as defined above for (I), M is Ti, Zr, Hf, V, Mn or Cr;

m is an integer equal to the valence of M minus 2; and each $L^1$ is independently a monodentate monoanionic ligand and at least for one of $L^1$ an ethylene molecule may insert between $L^1$ and M, and $L^2$ is a monodentate neutral ligand which may be displaced by ethylene or an empty coordination site, provided that an $L^1$ and $L^2$ taken together may be a monoanionic polydentate ligand and at least for one of these monoanionic polydentate ligands ethylene may insert between said monoanionic polydentate ligand and M.

In the above-mentioned processes, (V) and/or the transition metal complex of (I) may in and of themselves be active catalysts, or may be "activated" by contact with a cocatalyst/activator.

The present invention also concerns a compound of the formula (VI)

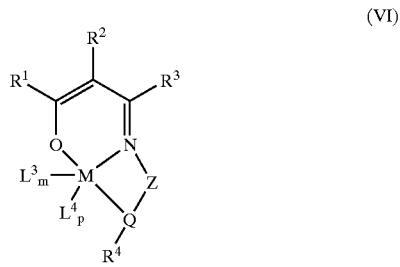

wherein $R^1$, $R^2$, $R^3$, $R^4$, Q, Z (and all R groups associated with Z), M and m are as defined above for (IV), p is 0 or 1; and each $L^3$ is independently a monodentate monoanionic ligand, and $L^4$ is a monodentate neutral ligand or an empty coordination site, provided that an $L^3$ and $L^4$ taken together may be a monoanionic bidentate ligand.

Further aspects of the present invention include, for example, the anion of the formula (I) as defined above, a Ti, Zr, Hf, V, Mn or Cr complex of such anion, and the combination of such complex, (V) and/or (VI) with a co-catalyst.

DETAILED DESCRIPTION OF THE PREFERRED EMBODIMENTS

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^{23}$ wherein $R^{23}$ is hydrocarbyl or substituted hydrocarbyl. In cases in which the functional group may be near a metal atom the functional group should not coordinate to the metal atom more strongly than the groups in those compounds are shown as coordinating to the metal atom, that is they should not displace the desired coordinating group.

By a "cocatalyst" or "catalyst activator" is meant one or more compounds that react with a transition metal compound to form an activated (or more active) catalyst species. A preferred catalyst activator is an "alkyl aluminum compound", that is, a compound which has at least one alkyl group bound to an aluminum atom. Other groups such as alkoxide, hydride, and halogen may also be bound to aluminum atoms in the compound.

By "neutral Lewis base" is meant a compound, which is not an ion, that can act as a Lewis base. Examples of such compounds include ethers, amines, sulfides and organic nitrites.

By "neutral Lewis acid" is meant a compound, which is not an ion, that can act as a Lewis acid. Examples of such compounds include boranes, alkylaluminum compounds, aluminum halides and antimony [V] halides.

By "cationic Lewis acid" is meant a cation that can act as a Lewis acid. Examples of such cations are sodium and silver cations.

By an "empty coordination site" is meant a potential coordination site on a metal atom that does not have a ligand bound to it. Thus if an ethylene molecule is in the proximity of the empty coordination site, the ethylene molecule may coordinate to the metal atom.

By a "ligand into which an ethylene molecule may insert" between the ligand and a metal atom, or a "ligand that may add to ethylene", is meant a ligand coordinated to the metal atom (which forms a bond L-M) into which an ethylene molecule (or a coordinated ethylene molecule) may insert to start or continue a polymerization. For instance, this may take the form of the reaction (wherein L is a ligand):

By a "ligand which may be displaced by ethylene" is meant a ligand coordinated to a transition metal, which when exposed to ethylene is displaced as the ligand by the ethylene.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By a "π-allyl group" is meant a monoanionic ligand with 1 $sp^3$ and two adjacent $sp^2$ carbon atoms bound to a metal center in a delocalized $\eta^3$ fashion. The three carbon atoms may be substituted with other hydrocarbyl groups or functional groups.

By "ortho-arylene" (or "o-arylene") is meant a divalent aryl group in which the free valencies are on adjacent carbon atoms. The o-arylene ring may be part of a fused and/or heterocyclic ring system and/or contain substituents such as hydrocarbyl groups or functional groups.

The polymerizations herein are carried out by a transition metal complex of anion (I). Many of the groups in (I) may have various forms, that is they may be "simple" groups such as hydrogen or alkyl, or they may participate in multiple bonds such as an imino bond to nitrogen or a carbon atom in an aromatic ring and/or they may be part of ring or ring systems. Some of these groups may optionally for instance be part of two different rings. Clearly simple valence rules are not broken in these anions and compounds, for example carbon will have a valence of 4. Thus if a particular group is part of one ring, it cannot be part of another ring or group that would violate these simple valence rules.

In order to illustrate this, and since (I) and its conjugate acid and transition metal complexes may have various individual structures, some of the conjugate acid structures are shown below, with certain salient features pointed out.

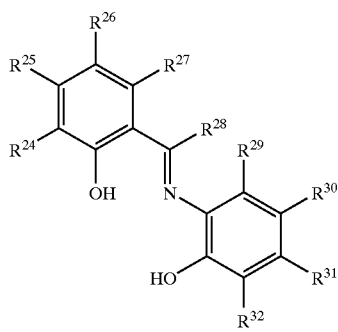

(VII)

In (VII), referring back to structure (I), $R^1$ and $R^2$ are taken together to form o-arylene (o-phenylene); $R^3$ is $R^{28}$; Z is (III); $R^6$, $R^7$, $R^8$ and $R^9$ are taken together to form an aromatic ring; and Q is oxygen. Generally in (VII), $R^{24}$, $R^{25}$, $R^{26}$, $R^{27}$, $R^{29}$, $R^{30}$, $R^{31}$ and $R^{32}$ are each independently hydrogen, hydrocarbyl, substituted hydrocarbyl or a functional group, and $R^{28}$ is hydrogen, hydrocarbyl or substituted hydrocarbyl, provided that any two of $R^{24}$, $R^{25}$, $R^{26}$, $R^{27}$, $R^{29}$, $R^{30}$, $R^{31}$ and $R^{32}$ vicinal to one another may be taken together to form a ring, and that $R^{27}$ and $R^{28}$ may be taken together to form a ring, or $R^{28}$ and $R^{29}$ may be taken together to form a ring.

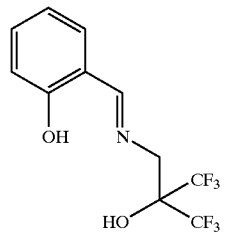

(VIII)

In (VIII), $R^1$ and $R^2$ are taken together to form o-arylene (o-phenylene); $R^3$ is hydrogen; Z is (III); $R^6$ and $R^7$ are hydrogen; $R^8$ and $R^9$ are trifluoromethyl; and Q is oxygen.

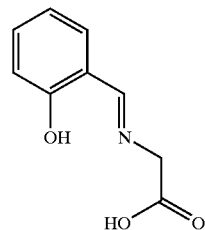

(IX)

In (IX), $R^1$ and $R^2$ are taken together to form o-arylene (o-phenylene); $R^3$ is hydrogen; Z is (III); $R^6$ and $R^7$ are hydrogen; $R^8$ and $R^9$ are taken together to form a carbonyl with the carbon to which they are attached; and Q is oxygen.

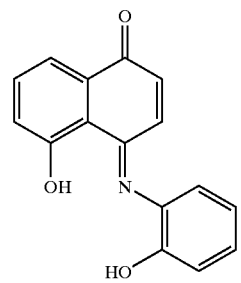

(X)

In (X), $R^1$, $R^2$ and $R^3$ are taken together to form a fused ring system, Z is (III), $R^6$, $R^7$, $R^8$ and $R^9$ are taken together to form an aromatic ring, and Q is oxygen.

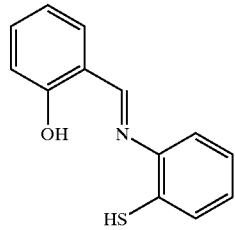

(XI)

In (XI), $R^1$ are $R^2$ are taken together to form o-arylene (o-phenylene); $R^3$ is hydrogen; Z is (III); $R^6$, $R^7$, $R^8$ and $R^9$ are taken together to form an aromatic ring; and Q is sulfur.

(XII)

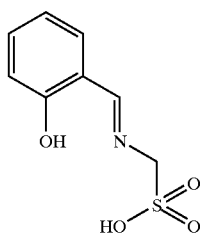

In (XII), $R^1$ and $R^2$ are taken together to form o-arylene (o-phenylene); $R^3$ is hydrogen; Z is (II); $R^{20}$ and $R^{21}$ are hydrogen; x is 4; T is sulfur; two each (twice) of $R^{22}$ are taken together to form S=O; and Q is oxygen.

(XIII)

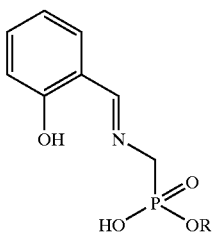

In (XIII), $R^1$ and $R^2$ are taken together to form o-arylene (o-phenylene); $R^3$ is hydrogen; Z is (II); $R^{20}$ and $R^{21}$ are hydrogen; x is 3; T is phosphorous; two of $R^{22}$ are taken together to form P=O; the other of $R^{22}$ is alkoxy; and Q is oxygen.

(XIV)

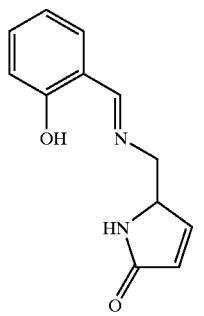

In (XIV), $R^1$ and $R^2$ are taken together to form o-arylene (o-phenylene); $R^3$ is hydrogen; Z is (III); $R^6$, $R^7$ and $R^8$ are hydrogen; $R^4$ and $R^9$ are taken together to form a ring; and Q is nitrogen.

(XV)

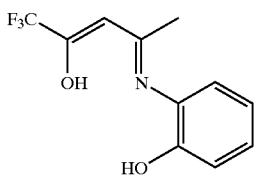

In (XV), $R^1$ is trifluoromethyl; $R^2$ is hydrogen; $R^3$ is methyl; Z is (III); $R^6$, $R^7$, $R^8$ and $R^9$ are taken together to form an aromatic ring; and Q is oxygen.

(XVI)

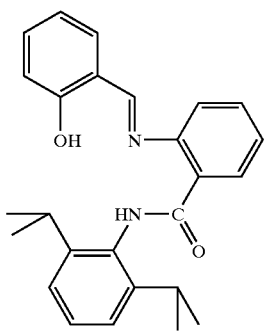

In (XVI), $R^1$ and $R^2$ are taken together to form o-arylene (o-phenylene); $R^3$ is hydrogen; Z is (IV); $R^{10}$, $R^{11}$, $R^{12}$ and $R^{13}$ are taken together form o-arylene; $R^{14}$ and $R^{15}$ are taken together together form a carbonyl with the carbon to which they are attached; $R^4$ is 2,6-di-iso-propylphenyl; and Q is nitrogen.

(XVII)

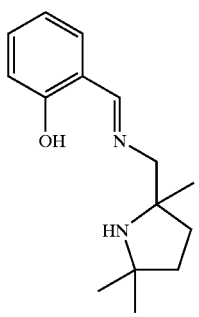

In (XVII), $R^1$ and $R^2$ are taken together to form o-arylene (o-phenylene); $R^3$ is hydrogen; Z is (III); $R^6$ and $R^7$ are hydrogen; $R^8$ is methyl; $R^4$ and $R^9$ are taken together to form a ring; and Q is nitrogen.

(XVIII)

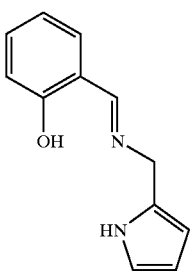

In (XVIII), $R^1$ and $R^2$ are taken together to form o-arylene (o-phenylene); $R^3$ is hydrogen; Z is (III); $R^6$, $R^7$ and $R^8$ are hydrogen; $R^4$ and $R^9$ are taken together to form a ring; and Q is nitrogen.

(XIX)

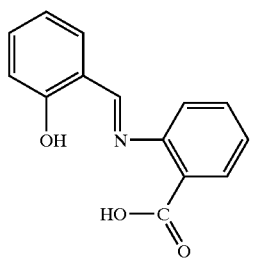

In (XIX), $R^1$ and $R^2$ are taken together to form o-arylene (o-phenylene); $R^3$ is hydrogen; Z is (IV); $R^{10}$, $R^{11}$, $R^{12}$ and $R^{13}$ are taken together to form o-arylene; $R^{14}$ and $R^{15}$ are taken together to form a carbonyl with the carbon to which they are attached; and Q is oxygen.

(XX)

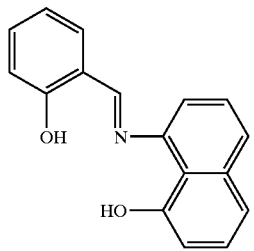

In (XX), $R^1$ and $R^2$ are taken together to form o-arylene (o-phenylene); $R^3$ is hydrogen; Z is (IV); $R^{10}$, $R^{11}$, $R^{12}$, $R^{13}$, $R^{14}$ and $R^{15}$ are taken together to form a fused aromatic ring system; and Q is oxygen.

(XXI)

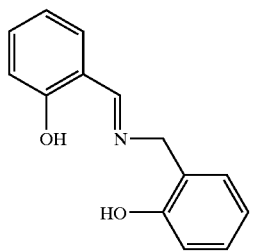

In (XXI), $R^1$ and $R^2$ are taken together to form o-arylene (o-phenylene); $R^3$ is hydrogen; Z is (IV); $R^{10}$ and $R^{11}$ are hydrogen; $R^{12}$, $R^{13}$, $R^{14}$ and $R^{15}$ are taken together to form an o-arylene group; and Q is oxygen.

In all of compounds (VII) through (XXI), groups and/or substituents may be changed where appropriate, for example methyl groups may be changed to other hydrocarbyl groups or hydrogen, hydrogen may be change to hydrocarbyl or functional groups.

A preferred anion (I), and all of its conjugate acid and metal complexes, is (VII), which is shown in the conjugate acid form. In its anion form, (VII) can be represented by the formula (XXVI)

(XXVI)

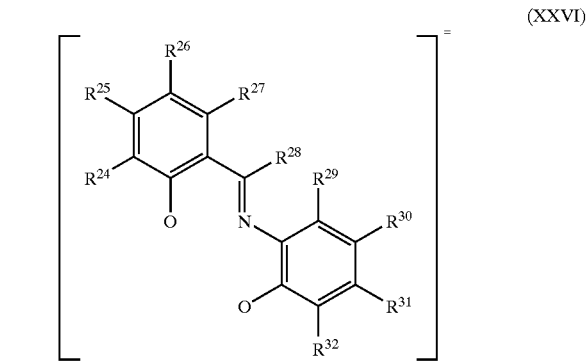

In its metal complex form, (VII) can be represented by the formulas (XXVII) and (XXVIII)

(XXVII)

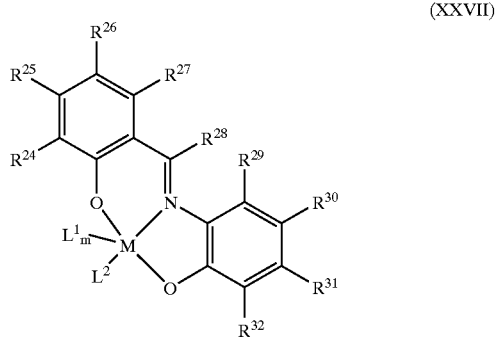

(XXVIII)

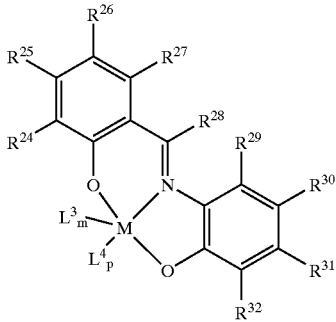

In (VII), (XXVI), (XXVII) and (XXVIII), it is preferred that:
  any or all of $R^{24}$ through $R^{32}$ are hydrogen; and/or
  $R^{24}$ and $R^{26}$ are nitro; and/or
  $R^{24}$ and $R^{26}$ are alkyls containing 1 to 6 carbon atoms, especially t-butyl;
  $R^{29}$ is an alkyl containing 1 to 6 carbon atoms, especially methyl; and/or
  $R^{26}$ and $R^{27}$ taken together form a n aromatic ring, expecially a 6-membered carbocyclic aromatic ring.

In preferred specific compounds of (VII), (XXVI), (XXVII) and (XXVIII), $R^{25}$, $R^{27}$, $R^{28}$, $R^{30}$, $R^{31}$ and $R^{32}$ are hydrogen, $R^{29}$ is methyl, and $R^{24}$ and $R^{26}$ are nitro; or $R^{25}$, $R^{27}$, $R^{28}$, $R^{30}$, $R^{31}$ and $R^{32}$ are hydrogen, $R^{29}$ is methyl, and $R^{24}$ and $R^{26}$ are t-butyl; or $R^{24}$, $R^{25}$, $R^{28}$, $R^{30}$, $R^{31}$ and $R^{32}$ are hydrogen, $R^{29}$ is methyl, and $R^{26}$ and $R^{27}$ taken together form a 6-membered carbocyclic aromatic ring.

The structure illustrated by (I) is not meant to preclude other tautomers, and all such tautomers are included herein.

For instance such structures (partial structures shown) may include:

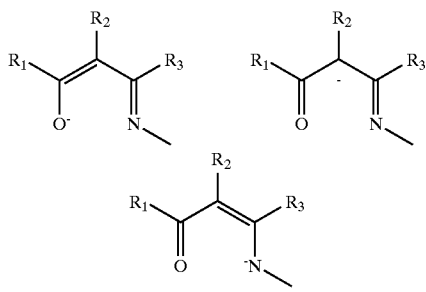

The conjugate acids of (I) can be made by a variety of methods, most of which are familiar to the skilled organic synthetic chemist, and which method(s) are chosen will depend on the particular structure desired, such as (VII) through (XXI). In all instances, if certain substituents/substitution patterns are desired, starting materials with those substituents/substitution patterns may be used. For example, (VII) may be made by reacting an appropriate salicylaldehyde with an appropriate 2-hydroxy-2-aminomethylpyridine. (VIII) may be made by reacting salicylaldehyde with 3,3,3-trifluoro-2-hydroxy-2-trifluoromethylpropylamine. (IX) can be made by reacting aminoacetic acid with salicylaldehyde. (X) can be made by reacting salicylaldehyde with 5-hydroxy-1,4-naphthalenedione. (XI) may be made by salicylaldehyde with 2-thioaniline. (XII) may be made by reacting salicylaldehyde with methyl aminomethyl sulfonate and hydrolyzing the resulting sulfonic ester-imine to the sulfonic acid-imine. (XIII) may be made by reacting salicylaldehyde with dimethyl aminomethyl phosphite and hydrolyzing the resulting phosphite diester-imine to the phosphite ester-acid-imine. (XIV) may be made by reacting salicylaldehyde with 4-aminomethyl-3-pyrrolin-2-one. (XV) may be made by reacting 1,1,1-trifluoro-2,5-pentanedione with 2-hydroxyaniline. (XVI) can be made by reacting o-aminobenzoic acid with salicylaldehyde, converting the resulting iminocarboxylic acid to the acyl halide and reacting the acyl halide with 2,6-diisopropylaniline. Some of these types of syntheses are also given in the Examples.

(I), the anion of the above conjugate acids, can be prepared by reaction of the conjugate acid with a strong base, such as an alkali metal hydride, an alkali metal alkoxide or a lithium disilylamide. It is preferred at this point that the cation(s) to this anion is an alkali metal cation, such as lithium, sodium and potassium. (I) may isolated as a salt and then used to form the transition metal compound, or may be formed and used in situ to produce the transition metal compound. The transition metal compound of (I) may be prepared by reacting (I) with an appropriate compound of the transition metal. For early transition metals such as Zr and Ti, the transition metal compound may be a halide such as $TiCl_4$ or $ZrCl_4$, in which case the ligands other than (I) attached to the metal will be halide such as chloride.

If (VI) is not already equivalent to (V), it may be converted to (V) before or during the polymerization process by reaction with other appropriate compounds (such as cocatalysts). Alternatively, the conjugate acid of (I) can be reacted with a transition metal compound such as $TiCl_4$, $TiCl_4 \cdot 2THF$ or $ZrCl_4$ in the presence of a base to neutralize the liberated hydrohalic acid.

In some of the structures written herein, such as (V) and (VI), it is not meant that (I) is a tridentate ligand, although it may be. The structures are written as they are for convenience, and to show that the anionic ligands (I) could be tridentate, but they may be only bidentate or even monodentate. Although it is believed in theory the ligands can be tridentate, the Applicants do not wish to be bound by this theory.

As implied above, (I) will normally be associated with a positively charged species, such as a cation. This may be a transition metal cation (as in (V)), or may be another cation such as an alkali metal cation.

In (V) useful groups $L^1$ include halide (especially chloride), hydrocarbyl and substituted hydrocarbyl (especially phenyl and alkyl, and particularly phenyl, methyl, hydride and acyl). Useful groups for $L^2$ include phosphine such as triphenylphosphine, nitrile such as acetonitrile, ethers such as ethyl ether, pyridine, and tertiary alkylamines such as triethylamine and TMEDA (N,N,N',N'-tetramethyl-1,2-ethylenediamine). Alternatively $L^1$ and $L^2$ taken together may be a π-allyl or π-benzyl group such as

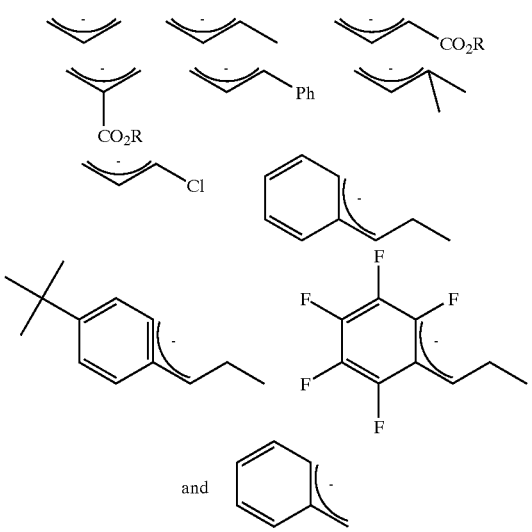

wherein R is hydrocarbyl, and π-allyl and π-benzyl groups are preferred.

In another variation, $L^3$ and $L^4$ taken together may be a β-diketonate ligand. If this ligand is present in (VI), it may be converted to (V) by use of a suitable alkylating agent such as an alkylaluminum compound, Grignard reagent or alkyllithium compound.

In (V) when ethylene may insert between $L^1$ and the transition metal atom, and $L^2$ is an empty coordination site or is a ligand which may be displaced by ethylene, or $L^1$ and $L^2$ taken together are a bidentate monoanionic ligand into which ethylene may be inserted between that ligand and the transition metal atom, (V) may by itself catalyze the polymerization of an olefin. Examples of $L^1$ which form bonds with the transition metal into which ethylene may insert are hydrocarbyl and substituted hydrocarbyl, especially phenyl and alkyl, and particularly methyl, hydride and acyl. Ligands $L^2$ which ethylene may displace include phosphine such as triphenylphosphine, nitrile such as acetonitrile, ether such as ethyl ether, pyridine, tertiary alkylamines such as TMEDA, and other olefins such as ethylene or isobutylene. Ligands in which $L^1$ and $L^2$ taken together are a monoanionic polydentate ligand into which ethylene may insert between that ligand and the transition metal atom include π-allyl- or π-benzyl-type ligands (in this instance, sometimes it may be necessary to add a neutral Lewis acid cocatalyst such as triphenylborane to initiate the polymerization, see for instance previously incorporated U.S. Pat. No. 6,174,975). For a summary of which ligands ethylene may insert into (between the ligand and transition metal atom) see, for instance, J. P. Collman, et al., *Principles and Applications of Organotransition Metal Chemistry*, University Science Book, Mill Valley, Calif., 1987, included herein by reference. If for instance $L^1$ is not a ligand into which ethylene may insert between it an the transition metal atom, it may be possible to add a cocatalyst which may convert $L^1$ into a ligand which will undergo such an insertion. Thus if $L^1$ is halo such as chloride or bromide, or carboxylate, it may be converted to hydrocarbyl such as alkyl by use of a suitable alkylating agent such as an alkylaluminum compound, a Grignard reagent or an alkyllithium compound. It may be converted to hydride by use of a compound such as sodium borohydride.

As indicated above, when $L^1$ and $L^2$ taken together are a monoanionic polydentate ligand, a cocatalyst (sometimes also called an activator) which is an alkylating or hydriding agent is also typically present in the olefin polymerization. A preferred cocatalyst is an alkylaluminum compound, and useful alkylaluminum compounds include trialkylaluminum compounds such as triethylaluminum, trimethylaluminum and tri-iso-butylaluminum, alkyl aluminum halides such as diethylaluminum chloride and ethylaluminum dichloride, and aluminoxanes such as methylaluminoxane. More than one such cocatalyst may be used in combination.

In (VI) in one preferred form at least one of $L^3$ is a ligand into which ethylene may insert between $L^3$ and the transition metal atom, and $L^4$ is an empty coordination site or a ligand which may be displaced by ethylene. In another preferred form of (VI), each of $L^3$ is a ligand into which ethylene may not insert between that ligand and the transition metal atom, such as halide, especially chloride, and carboxylate.

In the transition metal complexes of the present invention preferred metals are Ti and Zr. Generally speaking early transition metal complexes such as Ti and Zr produce polymers with the "expected" number and length of branches (see previously incorporated U.S. Pat. No. 5,880,241 for an explanation of "expected" branching). For example homopolyethylene will have essentially no branching (after correcting for-end groups), while poly(1-hexene) will have an n-butyl branch every other carbon atom (on average) of the main polymer chain.

A preferred olefin is ethylene, and when olefins other than ethylene are polymerized, it is preferred that they be copolymers with ethylene. In other preferred olefins n is 1 to 20.

In the polymerization processes herein, the temperature at which the polymerization is carried out is about −100° C. to about +200° C., preferably about −60° C. to about 150° C., more preferably about −20° C. to about 100° C. The pressure of the olefin (if it is a gas) at which the polymerization is carried out is not critical, atmospheric pressure to about 275 MPa being a suitable range.

The polymerization processes herein may be run in the presence of various liquids, particularly aprotic organic liquids. The catalyst system, monomer(s) and/or polymer may be soluble or insoluble in these liquids, but obviously these liquids should not prevent the polymerization from occurring. Suitable liquids include alkanes, cycloalkanes, selected halogenated hydrocarbons and aromatic hydrocarbons. Specific useful solvents include hexane, toluene, benzene methylene chloride, and 1,2,4-trichlorobenzene.

The olefin polymerizations herein may also initially be carried out in the "solid state" by, for instance, supporting the transition metal compound on a substrate such as silica or alumina, activating it if necessary with one or more cocatalysts and contacting it with the olefin(s). Alternatively, the support may first be contacted (reacted) with one or more cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle.

In all of the polymerization processes described herein oligomers and polymers of the various olefins are made. They may range in molecular weight from oligomeric POs (polyolefins), to lower molecular weight oils and waxes, to higher molecular weight POs. One preferred product is a polymer with a degree of polymerization (DP) of about 10 or more, preferably about 40 or more. By "DP" is meant the average number of repeat (monomer) units in a polymer molecule.

Depending on their properties, the polymers made by the processes described herein are useful in many ways. For instance if they are thermoplastics, they may be used as molding resins, for extrusion, films, etc. If they are elastomeric, they may be used as elastomers. See for instance previously incorporated U.S. Pat. No. 5,880,241.

Depending on the process conditions used and the polymerization catalyst system chosen, polymers, even those made from the same monomer(s) may have varying properties. Some of the properties that may change are molecular weight and molecular weight distribution.

It is known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers that inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. Monomers useful with these catalysts are those described (and also preferred) above. A second active polymerization catalyst (and optionally one or more others) is used in conjunction with the first active polymerization catalyst. The second active polymerization catalyst may be a transition metal catalyst, for example as described in previously incorporated U.S. Pat. No. 5,714,556, U.S. Pat. No. 5,880,241, U.S. Pat. No. 6,060,569 and U.S. Pat. No. 6,174,975, as well as U.S. Pat. No. 5,955,555 which is also incorporated by reference herein for all purposes as if fully set forth.

Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem.*, Int. Ed. Engl., vol. 34, p. 1143–1170 (1995), EP-A-0416815 and U.S. Pat. No. 5,198,401 for information about metallocene-type catalysts, and J. Boor Jr., *Ziegler-Natta Catalysts and Polymerizations,* Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (olefin(s) polymerized by the first active polymerization catalyst) and second olefin(s) (the monomer(s) polymerized by the second active polymerization catalyst) are identical. The second olefin may also be a single olefin or a mixture of olefins to make a copolymer.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer.

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may utilize a different ligand that differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this two catalyst process may vary in molecular weight and/or molecular weight distribution and/or melting point and/or level of crystallinity, and/or glass transition temperature and/or other factors. The polymers produced are useful as molding and extrusion resins and in films as for packaging. They may have advantages such as improved melt processing, toughness and improved low temperature properties.

Catalyst components which include transition metal complexes of (I), with or without other materials such as one or more cocatalysts and/or other polymerization catalysts are also disclosed herein. For example, such a catalyst component could include the transition metal complex supported on a support such as alumina, silica, a polymer, magnesium chloride, sodium chloride, etc., with or without other components being present. It may simply be a solution of the complex, or a slurry of the complex in a liquid, with or without a support being present.

In the Examples, all pressures are gauge pressures. Branching was determined by $^1$H NMR, taking the total of the methyl carbon atoms as the number of branches. Branching is uncorrected for end groups. Some of the transition metal complexes may have one or more molecules of THF coordinated per molecule of complex.

In the Examples, the following abbreviations are used:

ΔH—heat of fusion
Mn—number average molecular weight
Mw—weight average molecular weight
PE—polyethylene
PMAO—methylaluminoxane in toluene, 15.5 wt. % Al, from Akzo Chemicals, Inc.
RT—room temperature
THF—tetrahydrofuran
Tm—melting point by differential scanning calorimetry, taken as the peak of the melting endotherm at a heating rate of 10° C./min.

EXAMPLE 1

Synthesis of {[3',5'-(NO$_2$)$_2$-2'-OH]—(C$_6$H$_2$)} CH=N[(C$_6$H$_3$)-2-OH-6-Me]

A sample of 1.9901 g (9.38 mmol) of 3,5-dinitrosalicylaldehyde and a sample of 1.271 g (10.32 mmol) of 2-amino-m-cresol were placed in about 20 mL of methanol in a 100 mL flask and 5 drops of formic acid were added at RT. A yellow precipitate formed immediately. The reaction mixture was stirred overnight, then filtered to collect the yellow solid. Since the solid could not be dissolved in ether or methylene chloride or THF, it was rinsed with THF and dried under vacuo. A yellow powdery product (2.3338 g, 7.36 mmol) was obtained in 78% yield. $^1$H NMR (d$_8$-THF): 2.61 (s, 3H, CH$_3$), 6.87 (m, 2H, Ar—H), 7.13 (t, 1H, Ar—H), 8.69 (d, 1H, Ar—H), 8.81 (d, 1H, Ar—H), 9.56 (s, 1H, OH), 10.05 (s, 1H, OH), 10.82 (s, 1H, C—H).

EXAMPLE 2

Synthesis of {[3',5'-(t-Bu)$_2$-2'-OH]—(C$_6$H$_2$)} CH=N[(C$_6$H$_3$)-2-OH-6-Me]

A sample of 2.6122 g (11.15 mmol) of 3,5-di-tert-butylsalicylaldehyde and a sample of 1.5102 g (12.26 mmol)

of 2-amino-m-cresol were placed in about 20 mL of methanol in a 100 mL flask and 5 drops of formic acid were added at RT. The reaction mixture was stirred overnight, then filtered through Celite®. After removal of solvent, the orange oil residue was dissolved in ether and anhydrous sodium sulfate was added to the solution. After sodium sulfate and the solvent were removed, an orange oil was obtained, which was solidified later in a dry box freezer. A yellow solid (3.176 g, 9.36 mmol) was obtained in 84% yield. $^1$H NMR (CDCl$_3$): 1.25 (s, 9H, t-Bu), 1.41 (s, 9H, t-Bu), 2.19 (s, 3H, CH$_3$), 6.75 (d, 2H, Ar—H), 6.92 (t, 1H, Ar—H), 7.10 (d, 1H, Ar—H), 7.44 (d, 1H, Ar—H), 8.54 (s, 1H, C—H).

EXAMPLE 3

Synthesis of (2-OH—C$_{10}$H$_6$)CH=N[(C$_6$H$_3$)-2-OH-6-Me]

A sample of 4.122 g (0.024 mmol) of 2-hydroxy-1-naphthaldehyde and a sample of 3.833 g (0.0311 mmol) of 2-amino-m-cresol were placed in about 50 mL of methanol in a 250 mL flask and 5 drops of formic acid were added at RT. The reaction mixture was stirred 3 days and filtered to collect the yellow solid. Dried under vacuo, 5.7829 g (0.0208 mol) of yellow powder was obtained in 87% yield. It was insoluble in THF, CH$_2$Cl$_2$, ether and C$_6$H$_6$, so no NMR data are available.

EXAMPLE 4

Synthesis of Na$_2${{[3',5'-(NO$_2$)$_2$-2'-O]—(C$_6$H$_2$)}CH=N[(C$_6$H$_3$)-2-O-6-Me]}

In a dry-box, sodium hydride (0.65 g, 27 mmol) was slowly added to a flask containing a THF solution of the salicylaldimine (1.7028 g, 5.37 mmol) of Example 1. The reaction mixture was stirred overnight and filtered through a Celite® plug on the frit. The solvent was removed from the filtrate to yield dark-red solid product that was then rinsed with pentane and dried under vacuo. A dark-red powdery product (2.25 g, 5.61 mmol) was obtained in quantitative yield. $^1$H NMR (d$_8$-THF): 1.75 (m, CH$_2$-THF coordinated), 2.09 (s, 3H, CH$_3$), 3.58 (m, CH$_2$-THF coordinated), 6.00 (br, 1H, Ar—H), 6.12 (br, 1H, Ar—H), 6.5 (br, 1H, Ar—H), 8.16 (br, 1H, Ar—H), 8.34 (br, 1H, Ar—H), 8.55 (s, 1H, C—H).

EXAMPLE 5

Synthesis of Na$_2${{[3',5'-(t-Bu)$_2$-2'-O]—(C$_6$H$_2$)}CH=N[(C$_6$H$_3$)-2-O-6-Me]}

In a dry-box, sodium hydride (0.8569 g, 35.7 mmol) was slowly added to a flask containing a THF solution of the salicylaldimine (2.6934 g, 7.933 mmol). The reaction mixture was stirred 2 h and filtered through a Celite® plug on the frit. The solvent was removed from the filtrate to yield a greenish yellow solid product that was then rinsed with pentane and dried under vacuo. A greenish-yellow powder product (3.1428 g, 5.96 mmol) was obtained in 75% yield. $^1$H NMR (C$_6$D$_6$): 1.35 (m, CH$_2$-THF coordinated), 1.52 (s, 9H, t-Bu), 1.68 (br, 9H, t-Bu), 2.36 (br, 3H, CH$_3$), 3.58 (m, CH$_2$-THF coordinated), 6.68 (br, 2H, Ar—H), 7.0 (br, 1H, Ar—H), 7.18 (br, 1H, Ar—H), 7.60 (br, 1H, Ar—H), 8.45 (br, 1H, C—H).

EXAMPLE 6

Synthesis of Na$_2$(2-O—C$_{10}$H$_6$)CH=N[(C$_6$H$_3$)-2-O-6-Me]

In a dry-box, sodium hydride (0.4714 g, 19.64 mmol) was slowly added to a flask containing a THF suspension of the salicylaldimine (2.4758 g, 8.93 mmol). The reaction mixture was stirred 2 h and filtered through a Celite® plug on the frit. The solvent was removed from the filtrate to yield a yellow solid product that was then rinsed with pentane and dried under vacuo. Yellow crude product (3.223 g) was obtained. Recrystallized from a THF-pentane mixture, an orange crystalline solid was obtained. $^1$H NMR (C$_6$D$_6$-THF-d$_8$): 1.42 (m, CH$_2$-THF coordinated), 1.98 (br, 3H, CH$_3$), 3.48 (m, CH$_2$-THF coordinated), 6.38 (d, 1H, Ar—H), 6.48 (d, 1H, Ar—H), 6.62 (d, 1H, Ar—H), 6.90 (t, 1H, Ar—H), 7.16 (t, 1H, Ar—H), 7.30 (t, 1H, Ar—H), 7.35 (d, 1H, Ar—H), 7.44 (d, 1H, Ar—H), 7.65 (d, 1H, Ar—H), 8.45 (s, 1H, C—H).

EXAMPLE 7

Synthesis of {{[3',5'-(t-Bu)2-2'-O]—(C$_6$H$_2$)}CH=N[(C$_6$H$_3$)-2-O-6-Me]}TiCl$_2$:1

A. In a dry-box, a solution containing a sample of 0.7298 g (1.383 mmol) of the product of Example 5 in 20 mL of pentane was added dropwise to a precooled solution of TiCl$_4$ (0.2624 g, 1.383 mmol) in pentane at −30° C. A red brown solid formed and the reaction mixture was stirred 2 days, then the solvent was removed in vacuo. The residue was extracted with methylene chloride. After removal of the solvent, a dark brown powder (0.7406 g, 1.23 mmol) was obtained in 89% yield. $^1$H NMR (C$_6$D$_6$): 1.06 (s, 18H, t-Bu), 1.90 (s, 3H, CH$_3$), 6.3 (d, 1H, Ar—H), 6.55 (t, 1H, Ar—H), 6.8–7.0 (br, 3H, Ar—H), 7.41 (s, 1H, C—H). Another isomer: 1.16 (s, 18H, t-Bu), 1.82 (s, 3H, CH$_3$), 6.15 (d, 1H, Ar—H), 6.8–7.0 (br, 4H, Ar—H), 8.20 (s, 1H, C—H).

B. In a dry-box, a solution containing a sample of 0.2575 g (0.488 mmol) of the product of Example 5 in 20 mL of pentane was added dropwise to a pre-cooled solution of TiCl$_4$.(THF)$_2$ (0.1630 g, 0.488 mmol) in pentane at −30° C. A red brown solid formed and the reaction mixture was stirred 2 d, then the solvent was removed in vacuo. The residue was extracted with methylene chloride. After removal of the solvent, a dark red crystalline solid (0.221 g, 0.418 mmol) was obtained in 86% yield. $^1$H NMR (CD$_2$Cl$_2$): 1.39 (s, 9H, t-Bu), 1.52 (s, 9H, t-Bu), 1.90 (m, 4H, CH$_2$-THF coordinated), 2.54 (s, 3H, CH$_3$), 4.12 (m, 4H, CH$_2$-THF coordinated), 6.38 (d, 1H, Ar—H), 6.70 (br, H, Ar—H), 7.02 (br, 1H, Ar—H), 7.25 (br, 1H, Ar—H), 7.64 (br, 1H, Ar—H), 8.69 (br, 1H, C—H). The structure of the product was confirmed by X-ray for single crystal structure.

EXAMPLE 8

Synthesis of {{[3',5'-(t-Bu)$_2$-2'-O]—(C$_6$H$_2$)}CH=N[(C$_6$H$_3$)-2-O-6-Me]}ZrCl$_2$:2

A. In a dry-box, a solution containing a sample of 0.5462 g (1.035 mmol) of the product of Example 5 in 20 mL of pentane was added dropwise to a pre-cooled solution of ZrCl$_4$ (0.2412 g, 1.035 mmol) in pentane at −30° C. The yellow reaction mixture was stirred 3 days, then the solvent was removed in vacuo. The residue was extracted with toluene. After removal of the solvent, a yellow powder was obtained, 0.3009 g (0.602 mmol) in 58% yield. $^1$H NMR (C$_6$D$_6$): contained three different isomers and was very complicated.

B. In a dry-box, a solution containing a sample of 0.2558 g (0.485 mmol) of the product of Example 5 in 20 mL of pentane was added dropwise to a precooled solution of ZrCl$_4$ (THF)$_2$ (0.1829 g, 0.485 mmol) in pentane at −30° C. The yellow reaction mixture was stirred overnight, then the solvent was removed in vacuo. The residue was extracted with methylene chloride. After removal of the solvent and rinsing with pentane, a yellow solid was obtained, 0.166 g (0.332 mmol) in 69% yield.

EXAMPLE 9

Synthesis of {{[3',5'-(NO$_2$)$_2$-2'-O]—(C$_6$H$_2$)}CH=N[(C$_6$H$_3$)-2-O-6-Me]}TiCl$_2$:3

In a dry-box, a solution containing a sample of 0.1097 g (0.2736 mmol) of the product of Example 4 in 10 mL of methylene chloride was added dropwise to a precooled solution of TiCl$_4$ (0.0.0519 g, 0.2376 mmol) in 20 mL of pentane at −30° C. The red reaction mixture was stirred overnight and filtered through a Celite® plug on a frit, then the solvent was removed in vacuo. A dark red powder was obtained. $^1$H NMR (C$_6$D$_6$): it was a mixture of three different compounds.

EXAMPLE 10

Synthesis of {{[3',5'-(NO$_2$)$_2$-2'-O]—(C$_6$H$_2$)}CH=N[(C$_6$H$_3$)-2-O-6-Me]}ZrCl$_2$:4

In a dry-box, a solution containing a sample of 0.4775 g (1.191 mmol) of the product of Example 4 in 10 mL of toluene and THF (10:1) mixture was added dropwise to a precooled suspension of ZrCl$_4$ (0.2776 g, 1.191 mmol) in 20 mL of toluene at −30° C. The dark red reaction mixture was stirred 3 days and the solvents were removed under vacuo. The brown residue was extracted by methylene chloride. After the solvent was removed in vacuo, 0.1450 g of yellow orange powder was obtained, which was a very insoluble material, and therefore it was not be characterized by NMR.

EXAMPLE 11

Synthesis of {{[3',5'-(t-Bu)$_2$-2'-O]—(C$_6$H$_2$)}CH=N[(C$_6$H$_3$)-2-O-6-Me]}VCl$_2$:5

In a dry-box, a solution containing a sample of 0.5605 g (1.062 mmol) of the product of Example 5 in 20 mL of pentane was added dropwise to a pre-cooled suspension of VCl$_3$ (0.1671 g, 1.062 mmol) in 20 mL of pentane at −30° C. The dark red reaction mixture was stirred overnight and the solvent was removed under vacuo. The black residue was extracted by CH$_2$Cl$_2$ and THF. After the solvent was removed in vacuo, a golden yellow powder was obtained. $^1$H NMR (CD$_2$Cl$_2$): 1.25 (br, 9H, t-Bu), 1.34 (s, 9H, t-Bu), 1.81 (m, CH$_2$-THF coordinated), 2.41 (s, 3H, CH$_3$), 3.68 (m, CH$_2$-THF coordinated), 6.26 (d, 1H, Ar—H), 6.45 (br, 1H, Ar—H), 6.72 (br, 1H, Ar—H), 6.98 (br, 1H, Ar—H), 7.38 (br, 1H, Ar—H), 8.39 (very broad, 1H, C—H).

EXAMPLE 12

Synthesis of {{[3',5'-(t-Bu)$_2$-2'-O]—(C$_6$H$_2$)}CH=N[(C$_6$H$_3$)-2-O-6-Me]}HfCl$_2$:6

In a dry-box, a solution containing a sample of 0.1560 g (0.296 mmol) of the product of Example 5 in 20 mL of pentane was added dropwise to a precooled suspension of HfCl$_4$ (0.0947 g, 0.296 mmol) in pentane at −30° C. The yellow reaction mixture was stirred overnight, then the solvent was removed in vacuo. The residue was extracted with toluene. After removal of the solvent, a yellow powder was obtained. $^1$H NMR (C$_6$D$_6$): contained three different isomers and similar to its Zr analog.

EXAMPLE 13

Synthesis of {{[3',5'-(t-Bu)$_2$-2'-O]—(C$_6$H$_2$)}CH=N[(C$_6$H$_3$)-2-O-6-Me]}MnF:7

In a dry-box, a solution containing a sample of 0.0726 g (0.138 mmol) of the product of Example 5 in 10 mL of pentane was added dropwise to a precooled suspension of MnF$_3$ (0.0154 g, 0.138 mmol) in 10 mL of pentane at −30° C. The brown yellow reaction mixture was stirred 3 d, then the solvent was removed in vacuo. The residue was extracted with methylene chloride. After removal of the solvent, a brown yellow powder was obtained. $^1$H NMR (C$_6$D$_6$): very broad due to the paramagnetism of the product.

EXAMPLE 14

Synthesis of {{[3',5'-(t-Bu)$_2$-2'-O](C$_6$H$_2$)}CH=N[(C$_6$H$_3$)-2-O-6-Me]}CrCl.THF:8

In a dry-box, a solution containing a sample of 0.1214 g (0.23 mmol) of the product of Example 5 in 10 mL of pentane was added dropwise to a pre-cooled suspension of CrCl$_3$(THF)$_3$ (0.0862 g, 0.23 mmol) in 10 mL of pentane at −30° C. The reaction mixture with yellow solid was stirred 3 days, then the solvent was removed in vacuo. The residue was extracted with CH$_2$Cl$_2$. After removal of the solvent and rinsing with pentane, a brown powder was obtained. $^1$H NMR (C$_6$D$_6$): very broad due to the paramagnetism of the product.

EXAMPLE 15

Synthesis of (2-O—C$_{10}$H$_6$)CH=N[(C$_6$H$_3$)-2-O-6-Me]}TiCl$_2$:9

In a dry-box, a solution containing a sample of 0.094 g (0.284 mmol) of the product of Example 6 in 10 mL of methylene chloride was added dropwise to a pre-cooled solution of TiCl$_4$ (0.0.0519 g, 0.2376 mmol) in 20 mL of pentane at −30° C. The dark red reaction mixture was stirred overnight and filtered through a Celite® plug on a frit, washed with methylene chloride, and then the solvent was removed in vacuo. A dark red powder was obtained. $^1$H NMR (CD$_2$Cl$_2$): 1.71 (br, CH$_2$-THF coordinated), 2.63 (br, 3H, CH$_3$), 3.60 (br, CH$_2$-THF coordinated), 7.17 (d, 1H, Ar—H), 7.26 (m, 2H, Ar—H), 7.38 (t, 1H, Ar—H), 7.51 (d, 1H, Ar—H), 7.60 (d, 1H, Ar—H), 7.78 (t, 1H, Ar—H), 7.85 (d, 1H, Ar—H), 9.08 (d, 1H, Ar—H), 13.45 (s, 1H, C—H). There was another minor isomer present (1/5).

EXAMPLES 16–21

In a drybox, 0.02 mmol of the organometallic compound was placed in a Schlenk flask and 35 mL of toluene was added to dissolve or partially dissolve the compound. The flask was sealed, removed from the dry-box and attached to an ethylene line. After pumping off the air and nitrogen and purging with ethylene, 4.649 mL (20 mmol) of PMAO was quickly added to the flask under about 35 kPa ethylene. After being stirred at RT overnight, the reaction mixture was quenched with 50 mL of a methanol solution of concentrated HCl (10% volume). The polymer was collected on a frit, washed with methanol and acetone thoroughly, then dried in vacuo overnight. Results are given in Table 1.

TABLE 1

| Ex. | Organometallic Compound | PE (g) | Productivity (mol PE/ mol [Metal Cmpd] | Tm (° C.), ΔH (J/g) |
|---|---|---|---|---|
| 16 | 1 | 0.7817 | 1060 | 134.69, 174.5 |
| 17 | 2 | 0.2429 | 408 | 134.46, 188.9 |
| 18 | 3 | 0.3150 | 372 | 133.68, 174.4 |
| 19 | 4 | 0.0568 | 82 | 133.10, 147.5 |

EXAMPLES 22–35

In a dry-box, 0.02–0.01 mmol of the catalyst was placed in a glass vial and dissolved in 5 or 8.8 mL of 1,2,4- trichlorobenzene. The vial was cooled to −30° C. in a drybox freezer. PMAO (1.2 mL) was added to the vial on top of the frozen solution and the vial was then capped and sealed. Outside the drybox, the vials were placed into a shaker tube that was then shaken mechanically under certain pressure of ethylene for about 18 h. The reaction mixture was slowly poured into 100 mL of a methanol solution of concentrated HCl (10% volume). The mixture was stirred overnight and filtered. The polymer was collected on a frit, washed with acetone and dried in vacuo. Results are given in Table 2.

TABLE 2

| Ex. | Organometallic Compound | PE (g) | Productivity (mol PE/mol Metal Cmpd) | Tm (° C.), ΔH (J/g) | Temp. (° C.), Pressure (MPa) |
|---|---|---|---|---|---|
| 22 | 1 | 18.1725 | 4.83 × 10⁴ | 135.2, 150.8 | 25, 6.9 |
| 23 | 1 | 9.212 | 1.65 × 10⁴ | 132.6, 167.0 | 80, 6.9 |
| 24 | 1 | 0.6595 | 3700 | 133.27, 223.1 | 80, 1.9 |
| 25 | 2 | 10.5223 | 3.35 × 10⁴ | 137.71, 143.3 | 25, 6.9 |
| 25 | 2 | 7.9166 | 2.43 × 10⁴ | 137.09, 156.3 | 80, 6.9 |
| 26 | 2 | 2.297 | 9745 | 131.68, 206.4 | 80, 1.4 |
| 27 | 3 | 4.7633 | 1.45 × 10⁴ | 134.23, 132.6 | 80, 6.9 |
| 28 | 3 | 3.6587 | 8845.7 | 134.81, 120.0 | 25, 6.9 |
| 29 | 4 | 0.7999 | 2836 | 135.62, 153.4 | 25, 1.4 |
| 30 | 5 | 0.0515 | 142 | 131.82, 22.21 | 25, 3.5 |
| 31 | 5 | 0.0062 | 21 | | 25, 1.4 |
| 32 | 6 | 0.1654 | 461 | 134.81, 139.0 | 25, 1.4 |
| 33 | 7 | 0.0101 | 27 | | 25, 3.5 |
| 34 | 8 | 0.6168 | 1730 | 135.97, 109.0 | 25, 1.4 |
| 35 | 9 | 1.7619 | 6038 | 134.68, 111.0 | 25, 3.5 |

EXAMPLES 36–41

In a dry-box, 0.005 mmol of the catalyst was placed in a glass vial and dissolved in 3 mL of 1,2,4-trichlorobenzene. The vial was cooled to −30° C. in a drybox freezer. PMAO (500 equiv.) and 1-hexene then were added to the vial on top of the frozen solution and the vial was then capped, sealed and placed into a shaker tube which was then shaken mechanically under 1.4 MPa ethylene for about 18 h. The reaction mixture was slowly poured into 100 mL of a methanol solution of concentrated HCl (10% volume). The mixture was stirred overnight and filtered. The polymer was collected on a frit, washed with acetone and dried in vacuo. The molecular weight was unmeasurable because of poor solubility of the polymer in trichlorobenzene. Results are given in Table 3.

TABLE 3

| Ex. | Organometallic Compound | Copolymer (g) | Productivity (kg Polymer/mol Metal Cmpd) | Tm (° C.), ΔH (J/g) | Me/1000 CH₂ ¹H NMR (d₂-TCE) |
|---|---|---|---|---|---|
| 36 | 1 | 2.698 | 492.4 | 129.45, 106.4 | 22.39 |
| 37 | 2 | 1.5921 | 248.6 | 127.48, 109.9 | 21.0 |
| 38 | 3 | 1.0719 | 122.4 | 119.21, 129.32 | 51.07 |
| 39 | 4 | 0.1915 | 26.12 | 130.70, 108.9 | 25.47 |
| 40 | 8 | 0.3938 | 42.91 | | 19.13 |
| 41 | 9 | 0.2143 | 46.92 | | 87.28 |

EXAMPLES 42–43

In a dry-box, 0.02 mmol of the catalyst and 7.66 mL of toluene were placed in a 20 mL glass vial. Three mL of 1-hexene were added to the vial. Then, 2.34 mL (10 mmol) of PMAO was quickly added to the vial. After being stirred at RT 48 h, the reaction mixture was taken from the drybox and slowly poured to a beaker containing 50 mL of a methanol solution of concentrated HCl (10% volume). The colorless waxy polymer was separated from the methanol solution, washed with methanol and acetone thoroughly and then dried in vacuo overnight. Results are given in Table 4.

TABLE 4

| Ex. | Organometallic Compound | Polymer (g) | Productivity | Mw (Mw/Mn) |
|---|---|---|---|---|
| 42 | 1 | 0.2215 | 112 | 531 (4.14) |
| 43 | 2 | 0.0186 | 9 | |

What is claimed is:
1. A compound of the formula (VI)

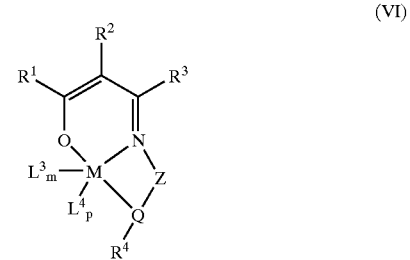

wherein:
$R^1$ is hydrocarbyl or substituted hydrocarbyl, $R^2$ is hydrogen, hydrocarbyl or substituted hydrocarbyl, and $R^3$ is hydrogen, hydrocarbyl, substituted hydrocarbyl or a functional group, provided that $R^1$ and $R^2$ taken together may be ortho-arylene or substituted ortho-arylene, or $R^1$, $R^2$ and $R^3$ taken together may form one or more rings;
Z is a bridging group of the formula (II), (III) or (IV)

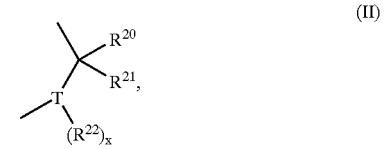

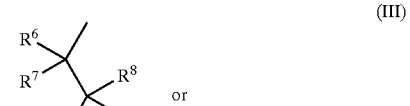

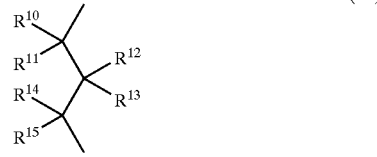

Q is nitrogen, oxygen, phosphorous or sulfur, provided that when Z is (II), Q is oxygen;
$R^4$ is hydrogen, hydrocarbyl or substituted hydrocarbyl, provided that when Q is oxygen or sulfur $R^4$ is not present;
$R^6$ is hydrogen, hydrocarbyl or substituted hydrocarbyl, provided that $R^3$ and $R^6$ taken together may form a ring;

$R^7$ is hydrogen, hydrocarbyl or substituted hydrocarbyl, provided that $R^3$, $R^6$ and $R^7$ taken together may form an aromatic ring, or $R^6$ and $R^7$ taken together may form a ring;

$R^8$ is hydrogen, hydrocarbyl or substituted hydrocarbyl;

$R^9$ is hydrogen, hydrocarbyl or substituted hydrocarbyl, provided that $R^4$ and $R^9$ taken together may be part of a double bond to an imino nitrogen atom, or $R^8$ and $R^9$ taken together may form a carbonyl with the carbon to which they are attached, or $R^8$ and $R^9$ taken together may form a ring, or $R^4$ and $R^9$ taken together may form a ring, or $R^4$, $R^8$ and $R^9$ taken together may form a ring, or $R^6$, $R^7$, $R^8$ and $R^9$ taken together may form an aromatic ring;

$R^{10}$, $R^{11}$, $R^{12}$ and $R^{13}$ are each independently hydrogen, hydrocarbyl or substituted hydrocarbyl, provided that $R^{10}$, $R^{11}$, $R^{12}$ and $R^{13}$ taken together may be ortho-arylene;

$R^{14}$ and $R^{15}$ are each independently hydrogen, hydrocarbyl or substituted hydrocarbyl, provided that $R^{14}$ and $R^{15}$ taken together may form a carbonyl with the carbon to which they are attached, or $R^{12}$, $R^{13}$, $R^{14}$, and $R^{15}$ taken together may form an o-arylene group, or $R^{10}$, $R^{11}$, $R^{12}$, $R^{13}$, $R^{14}$, and $R^{15}$ taken together may form a fused aromatic ring system, or $R^{13}$ and $R^{14}$ taken together may form a ring;

$R^{20}$ and $R^{21}$ are each independently hydrogen, hydrocarbyl or substituted hydrocarbyl, or $R^{20}$ and $R^{21}$ taken together may form a ring;

each $R^{22}$ is individually hydrocarbyl, oxygen or alkoxy, provided that when $R^{22}$ is oxygen, two of $R^{22}$ are taken together to form T=O;

n is an integer of 1 or more;

T is phosphorous or sulfur whose oxidation state is 3 or greater;

x is equal to the oxidation state of T minus 2;

M is Zr, Hf, Mn or Cr;

m is an integer equal to the valence of M minus 2; and p is 0 or 1; and each $L^3$ is independently a monodentate monoanionic ligand, and $L^4$ is a monodentate neutral ligand or an empty coordination site, provided that an $L^3$ and $L^4$ taken together may be a monoanionic bidentate ligand.

2. The compound as recited in claim 1, wherein M is Zr.

3. The compound as recited in claim 1, wherein $R^1$ and $R^2$ taken together are o-arylene, Z is a group of the formula (III), Q is oxygen, and $R^6$, $R^7$, $R^8$ and $R^9$ taken together form an aromatic ring.

4. The compound as recited in claim 1, wherein (VI) has the formula

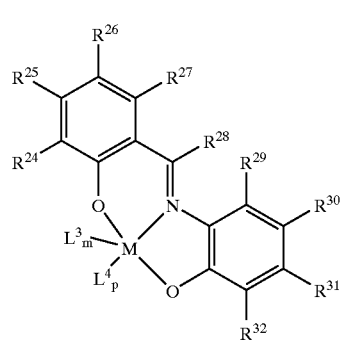

(XXVIII)

wherein $R^{24}$, $R^{25}$, $R^{26}$, $R^{27}$, $R^{29}$, $R^{30}$, $R^{31}$ and $R^{32}$ are each independently hydrogen, hydrocarbyl, substituted hydrocarbyl or a functional group, and $R^{28}$ is hydrogen, hydrocarbyl, or substituted hydrocarbyl, provided that any two of $R^{24}$, $R^{25}$, $R^{26}$, $R^{27}$, $R^{29}$, $R^{30}$, $R^{31}$ and $R^{32}$ vicinal to one another may be taken together to form a ring, and that $R^{27}$ and $R^{28}$ may be taken together to form a ring, or $R^{28}$ and $R^{29}$ may be taken together to form a ring.

* * * * *